United States Patent
Matsuda et al.

(10) Patent No.: US 8,518,995 B2
(45) Date of Patent: Aug. 27, 2013

(54) METHODS AND COMPOSITIONS FOR THE TREATMENT OF IRRITABLE BOWEL SYNDROME

(75) Inventors: Kazuko Matsuda, Beverly Hills, CA (US); Yuichi Iwaki, Palos Verdes Estates, CA (US); Kale Ruby, Encinitas, CA (US)

(73) Assignee: MediciNova, Inc., San Diego, CA (US)

( * ) Notice: Subject to any disclaimer, the term of this patent is extended or adjusted under 35 U.S.C. 154(b) by 3 days.

(21) Appl. No.: 13/079,566

(22) Filed: Apr. 4, 2011

(65) Prior Publication Data

US 2011/0319490 A1 Dec. 29, 2011

Related U.S. Application Data

(60) Provisional application No. 61/322,201, filed on Apr. 8, 2010.

(51) Int. Cl.
| | | |
|---|---|---|
| A61K 31/196 | (2006.01) | |
| A61K 31/165 | (2006.01) | |
| A61P 1/00 | (2006.01) | |
| A61P 29/00 | (2006.01) | |
| A61P 31/00 | (2006.01) | |
| A61P 25/24 | (2006.01) | |
| A61P 23/02 | (2006.01) | |
| A61P 1/10 | (2006.01) | |
| A61P 1/12 | (2006.01) | |
| A61P 13/06 | (2006.01) | |
| A61P 1/14 | (2006.01) | |

(52) U.S. Cl.
USPC .......... 514/567; 514/620; 564/165; 564/167; 564/171; 564/172; 562/400; 562/405

(58) Field of Classification Search
USPC ................. 514/567, 620; 564/165, 167, 171, 564/172; 562/400, 405
See application file for complete search history.

(56) References Cited

U.S. PATENT DOCUMENTS

| 6,133,266 A | 10/2000 | Kitazawa et al. |
| 6,136,852 A * | 10/2000 | Kitazawa et al. .......... 514/510 |
| 6,696,486 B1 | 2/2004 | Bahl |

FOREIGN PATENT DOCUMENTS

EP 0 822 185 2/1998

OTHER PUBLICATIONS

Definition of Prevent, Princeton University "About WordNet." WordNet. Princeton UNiversity. 2010. <http://wordnet.princeton.edu>, accessed Sep. 18, 2012.*
Drossman et al. Gastroenterology 2002, 123, 2108-2131.*
Stella et al. Prodrugs: Challenges and Rewards, Springer New York 2007.*
Elliott et al. American Journal of Obstetrics and Gynecology 2004, 191, 1277-1282.*
Lyrenas et al. Scand. J. Gastroenterol. 1985, 20, 1163-1168.*
Basilisco et al., "Single doses of ritodrine delay orocaecal transit in patients with irritable bowel syndrome", Br. J. Clin. Pharmac. 1990, vol. 29, pp. 355, 357, 358.
International Search Report in PCT/US2011/31066 dated Jun. 1, 2011.

* cited by examiner

*Primary Examiner* — Sreeni Padmanabhan
*Assistant Examiner* — Irina Neagu
(74) *Attorney, Agent, or Firm* — Gilberto M. Villacorta; Photon Rao; Foley & Lardner LLP

(57) ABSTRACT

A method for a prevention and/or treatment of irritable bowel syndrome or amelioration of a symptom thereof in a subject, comprises administering to said subject an effective amount of a compound of formula I:

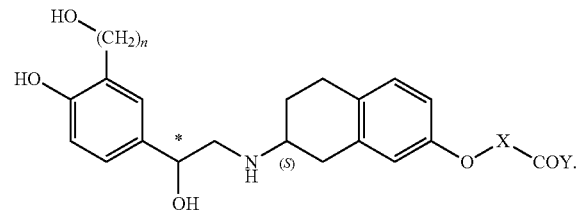

19 Claims, No Drawings

METHODS AND COMPOSITIONS FOR THE TREATMENT OF IRRITABLE BOWEL SYNDROME

RELATED APPLICATIONS

This application claims priority to U.S. provisional application No. 61/322,201 filed on Apr. 8, 2010, which is incorporated herein by reference.

FIELD OF THE INVENTION

The present technology relates to compositions, devices and methods for the treatment of irritable bowel syndrome and is generally related to the field of medicine, pharmacology, molecular biology, and chemistry.

BACKGROUND OF THE INVENTION

Irritable bowel syndrome (IBS) is one of the common ailments of the bowel (intestines) and affects an estimated 15% of people in the US. Other names for IBS include, but are not limited to, spastic colon, spastic colitis, and mucous colitis.

IBS may be due to the abnormal function of the muscles of the organs of the gastrointestinal tract or the nerves controlling the organs. The abnormal function of the nervous system in IBS may occur in a gastrointestinal muscular organ, the spinal cord, or the brain. The abnormalities may occur in the sensory nerves, the motor nerves, or at processing centers in the intestine, spinal cord, or brain. Normal activities, such as stretching of the small intestine by food, may give rise to abnormal sensory signals that are sent to the spinal cord and brain, where they are perceived as pain. Abnormal commands through the motor nerves may also produce a painful spasm (contraction) of the muscles. Therefore, IBS may be due to sensory dysfunction, motor dysfunction, or both sensory and motor dysfunction.

IBS normally causes cramping, abdominal pain, bloating, constipation, diarrhea, etc. IBS may not lead to more serious conditions in most patients, but it is a source of chronic pain, fatigue and other symptoms. It increases a patient's medical cost and may contribute to work absenteeism. The high prevalence of IBS in conjunction with increased costs may produce a disease with a high societal cost. It is also regarded as a chronic illness and can dramatically affect the quality of a sufferer's life.

Thus, there exists a need for an effective and safe treatment of irritable bowel syndrome.

SUMMARY OF THE INVENTION

Disclosed herein are methods, compositions, and devices for the treatment of irritable bowel syndrome.

In one aspect, there is provided a method for a prevention and/or treatment of irritable bowel syndrome or amelioration of a symptom thereof in a subject, comprising administering to said subject an effective amount of a compound of formula I:

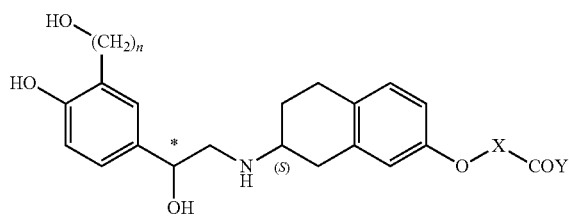

wherein
n is an integer selected from 1 or 2;
X is a $C_1$-$C_6$ alkylene group;
Y is —$N(R)_2$ wherein each R is independently selected from hydrogen or $C_1$-$C_6$ alkyl, or two R along with the nitrogen bound thereto join together to form a 3 to 7 membered heterocyclic ring optionally containing an oxygen atom; and
* represents a carbon atom in an R configuration, an S configuration, or a mixture thereof, a metabolite thereof, a prodrug thereof, or a pharmaceutically acceptable salt of any of the foregoing.

In one aspect, there is provided a method for a prevention and/or treatment of irritable bowel syndrome or amelioration of a symptom thereof in a subject, comprising administering to said subject an effective amount of a compound of formula V:

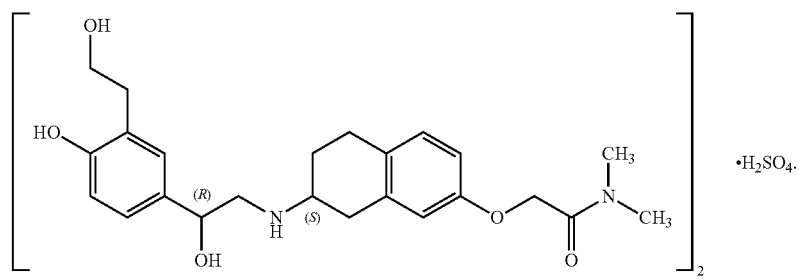

DETAILED DESCRIPTION OF THE INVENTION

1. Definitions

It must be noted that as used herein, and in the appended claims, the singular forms "a," "an" and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

An "administration" or "administering," refers to the delivery of a medication, such as the composition of the invention to an appropriate location of the subject or in vitro, where a desired effect is achieved. Non-limiting examples include topical, oral, parenteral, direct application to target area or proximal areas on the skin, or applied transdermally such as a patch. Various physical and/or mechanical technologies are available to permit the sustained or immediate release of the composition after administration.

A "$C_1$-$C_6$ alkyl" refers to saturated monovalent hydrocarbyl groups having from 1 to 6 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl and the like.

A "$C_1$-$C_6$ alkylene" refers to divalent saturated aliphatic hydrocarbyl groups having from 1 to 6 carbon atoms and, in some embodiments, from 1 to 3 carbon atoms. The alkylene groups include branched and straight chain hydrocarbyl groups. Examples include methylene (—$CH_2$—), ethylene, propylene, 2-methypropylene, pentylene and the like.

A "compound" herein refers to a compound utilized according to the invention, a pharmaceutically acceptable salt thereof, a metabolite thereof, a prodrug thereof, a pharmaceutically acceptable salt of the metabolite thereof, or a pharmaceutically acceptable salt of the prodrug thereof. The compounds include stereoisomeric forms and the tautomeric forms of the compounds.

A "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

An "effective amount" or a "therapeutically effective amount" is an amount sufficient to effect beneficial or desired results, e.g., alleviation, amelioration, palliation or elimination of one or more manifestations of IBS in the subject. The full therapeutic effect may occur in one dose; may not necessarily occur by administration of one dose (or dosage); and may occur only after administration of a series of doses. Thus, a therapeutically effective amount may be administered in one or more administrations, applications or dosages.

A "heterocycle" or "heterocyclic" refers to a saturated or unsaturated (but not aromatic) group having a single ring or multiple condensed rings, from 3 to 6 carbon atoms, and from 1 to 4 hetero atoms selected from the group consisting of nitrogen or oxygen within the ring wherein, in fused ring systems, one or more of the rings can be aryl or heteroaryl provided that the point of attachment is at the heterocycle. The nitrogen ring atoms can optionally be oxidized to provide for the N-oxide derivatives. Examples of heterocycles include, but are not limited to, azetidine, pyrrole, imidazole, pyrazole, pyridine, pyrazine, pyrimidine, pyridazine, etc.

A "metabolite" refers to any substance that is produced as an intermediate or a product after the metabolism of the compound utilized according to the invention. Examples of metabolites include, but are not limited to, acid metabolized from the amide moiety, amine metabolized from the substituted amide moiety, alcohol metabolized from alkoxy moiety, and the like. A representative carboxylic acid metabolite, is described in U.S. Pat. No. 6,136,852, the disclosure of which is incorporated herein by reference in its entirety.

A "subject" or "patient" is a female or male mammal, including a human. Non-human animals subject to diagnosis or treatment include, for example, murine, such as rats, mice, canine, such as dogs, leporids, such as rabbits, livestock, sport animals, and pets.

A "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co., Easton (1975)). The term includes carriers that facilitate controlled release of the active agent as well as immediate release.

A "pharmaceutically acceptable salt" refers to pharmaceutically acceptable salts of a compound, which salts are derived from a variety of organic, and inorganic counter ions well known in the art. When the molecule contains a basic functionality, salts include, by way of example only, sodium, potassium, calcium, magnesium, ammonium, tetraalkylammonium, and the like. When the molecule contains a basic functionality, salts of organic or inorganic acids include, such as hydrochloric, sulfuric, phosphoric, acetic, citric, oxalic, malonic, salicyclic, malic, gluconic, fumaric, succinic, ascorbic, maleic, methanesulfonic acid, etc.

A "prodrug", as used herein, refers to any covalently bonded carrier which releases the active parent drug in vivo when such prodrug is administered to a subject. Prodrugs of a compound are prepared by modifying functional groups present in the compounds in such a way that the bonds are cleaved, either in routine manipulation or in vivo, to the parent compounds. Prodrugs include, but are not limited to, compounds wherein hydroxyl or amine groups are bonded to any group that, when administered to a subject, cleave to form a free hydroxyl or amino, group, respectively. Examples of prodrugs include, but are not limited to, acetate, formate, benzoate and phosphate ester derivatives of hydroxyl functional groups, especially the hydroxyl group on the phenyl ring of formula I, and acetyl and benzoyl derivatives of amine functional groups in the compounds utilized according to the invention and the like.

A "treating," "treatment" and the like refer to obtaining a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to the disorder. Examples of "treatment" include but are not limited to: preventing a disease from occurring in a subject that may be predisposed or at risk of a disease, but has not yet been diagnosed as having it; inhibiting a disease, i.e., arresting its development; and/or relieving or ameliorating the symptoms of disease or reducing the likelihood of recurrence of the disease, such as IBS. As is understood by those skilled in the art, "treatment" can include systemic amelioration of the symptoms associated with the pathology and/or a delay in onset of symptoms.

2. Methods of the Invention

In one aspect, there is provided a method for a prevention and/or treatment of irritable bowel syndrome or amelioration of a symptom thereof in a subject, comprising administering to the subject an effective amount of a compound, as provided herein.

Irritable bowel syndrome (IBS or spastic colon) may be a functional bowel disorder characterized by chronic abdominal pain, discomfort, bloating, and alteration of bowel habits. In some cases, the symptoms are relieved by bowel movements. Diarrhea or constipation may be a predominant symptom of IBS that may alternate in the patient, i.e., an incidence of diarrhea may be followed by an incidence of constipation which may be followed by an incidence of diarrhea. IBS may begin after an infection, a stressful life event, or onset of maturity without any other medical indicators.

IBS may be classified as either diarrhea-predominant (IBS-D), constipation-predominant (IBS-C) or IBS with alternating stool pattern (IBS-A or pain-predominant). In some subjects, IBS may have an acute onset and develop after an infectious illness characterized by two or more of the following: fever, vomiting, diarrhea, or positive stool culture. This post-infective syndrome is called "post-infectious IBS" (IBS-PI). Several other conditions may be related to IBS including, but are not limited to, celiac disease, mild infections, parasitic infections like giardiasis, inflammatory bowel disease, functional chronic constipation, and chronic functional abdominal pain. It is to be understood that the treatment of IBS disclosed herein, includes the treatment of various types of IBS, symptoms of IBS, and other secondary diseases caused by or related to IBS.

The common symptoms of IBS resemble symptoms of other conditions or medical problems, such as, but are not limited to, nausea, vomiting, diarrhea, constipation, abdominal bloating (the sensation of abdominal fullness), flatulence, abdominal distention (enlargement), and pain. The symptom of rapid transportation of food may be diarrhea and slow transportation of food may be constipation. In addition, there may be increased amounts of mucus coating the stool or a sense of incomplete evacuation after a bowel movement.

IBS may be diagnosed based on the symptoms, including the frequency of the abdominal pain or discomfort during the past year or month or week; the beginning and the end of the pain in relation to bowel function; and the change in the bowel frequency and stool consistency. Several diagnostic tests may be performed to diagnose IBS. These tests include, but are not limited to, stool sample testing, blood tests, x-rays, endoscopy such as, sigmoidoscopy, colonoscopy, etc., abdominal ultrasonography (US), computerized tomography (CT or CAT scans), or magnetic resonance imaging (MRI).

The dosage and the regimen for the treatment for IBS using the compositions and methods of the invention can depend on age, overall health, and medical history; extent of the condition; cause of the condition (primary or secondary); and tolerance for specific medications, procedures, or therapies.

Accordingly, in some embodiments, there is provided a method for a prevention and/or treatment of irritable bowel syndrome or amelioration of a symptom thereof in a subject, comprising administering to said subject an effective amount of a compound of formula I:

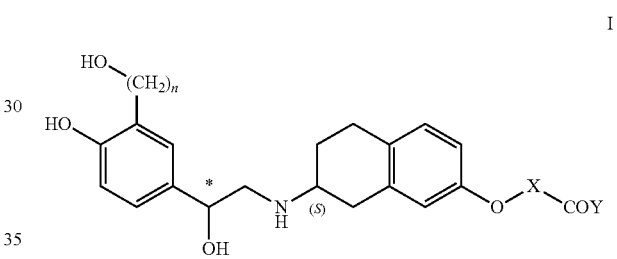

wherein
n is an integer selected from 1 or 2;
X is a $C_1$-$C_6$ alkylene group;
Y is —$N(R)_2$ wherein each R is independently selected from hydrogen or $C_1$-$C_6$ alkyl, or two R along with the nitrogen bound thereto join together to form a 3 to 7 membered heterocyclic ring optionally containing an oxygen atom; and
* represents a carbon atom in an R configuration, an S configuration, or a mixture thereof,
a metabolite thereof, a prodrug thereof, or a pharmaceutically acceptable salt of any of the foregoing.

In some embodiments, there is provided a method for a prevention and/or treatment of irritable bowel syndrome or amelioration of a symptom thereof in a subject, comprising administering to said subject an effective amount of a compound of formula II:

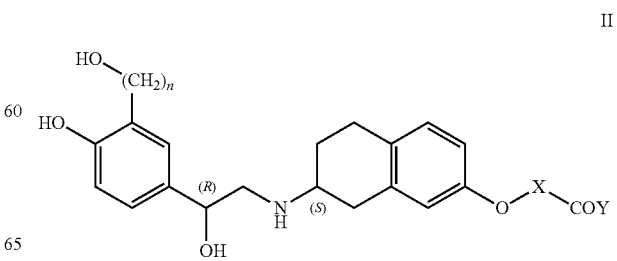

wherein
  n is an integer selected from 1 or 2;
  X is a $C_1$-$C_6$ alkylene group; and
  Y is —$N(R)_2$ wherein each R is independently selected from hydrogen or $C_1$-$C_6$ alkyl, or two R along with the nitrogen bound thereto join together to form a 3 to 7 membered heterocyclic ring optionally containing an oxygen atom;

\* represents a carbon atom in an R configuration, an S configuration, or a mixture thereof, or a pharmaceutically acceptable salt thereof.

In some embodiments, there is provided a method for a prevention and/or treatment of irritable bowel syndrome or amelioration of a symptom thereof in a subject, comprising administering to said subject an effective amount of a compound of formula V:

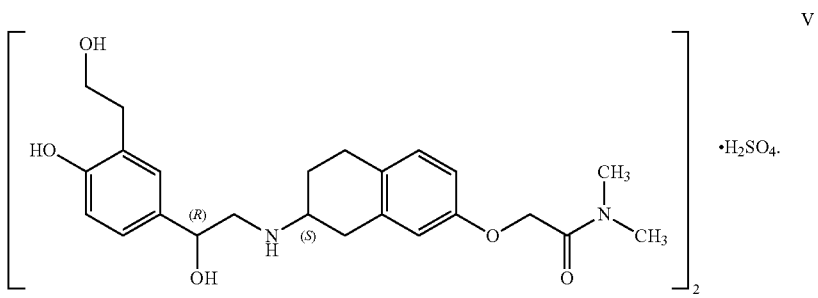

a metabolite thereof, a prodrug thereof, or a pharmaceutically acceptable salt of any of the foregoing.

In some embodiments, there is provided a method for a prevention and/or treatment of irritable bowel syndrome or amelioration of a symptom thereof in a subject, comprising administering to said subject an effective amount of a compound of formula III:

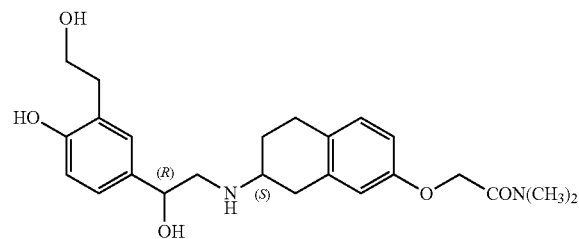

a metabolite thereof, a prodrug thereof, or a pharmaceutically acceptable salt of any of the foregoing.

In some embodiments, there is provided a method for a prevention and/or treatment of irritable bowel syndrome or amelioration of a symptom thereof in a subject, comprising administering to said subject an effective amount of a metabolite of formula IV:

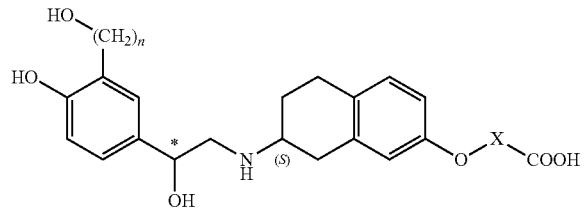

wherein
  n is an integer selected from 1 or 2;
  X is a $C_1$-$C_6$ alkylene group; and In one aspect, the present invention provides a method for treating a human subject suffering from irritable bowel syndrome. In some embodiments, the human subject is female. In some embodiments, the human subject is male.

The treatments that may be used in conjunction with the methods of the invention to relieve symptoms of IBS, include, but are not limited to, dietary adjustments, drugs and psychological interventions. The drugs include, but are not limited to, such as laxatives, anti-diarrhea medicines, anti-spasmodics, or anti-depressants.

In some embodiments, the methods provided herein further comprise administering to the subject one or more of a drug selected from the group consisting of non-steroidal anti-inflammatory drug, antibiotic, probiotics, anti-prostaglandin, COX-2 inhibitor, local anesthetic, laxative, anti-diarrhea medicine, anti-spasmodic, and anti-depressant. The methods of the invention may be accompanied with life style changes such as, reduced stress, exercise, and change in the diet.

Non-limiting examples of non-steroidal anti-inflammatory drugs suitable for use in the method of the invention include, but are not limited to, aspirin, ibuprofen, indomethacin, phenylbutazone, bromfenac, fenamate, sulindac, nabumetone, ketorolac, and naproxen. Examples of antibiotics include, but are not limited to, rifaximin and neomycin. Examples of probiotics include, but are not limited to, VSL#3, Flora-Q or *bifidobacterium infantis* 35624. Examples of local anesthetics include, but are not limited to, lidocaine, mepivacaine, etidocaine, bupivacaine, 2-chloroprocaine hydrochloride, procaine, and tetracaine hydrochloride. Examples of COX-2 inhibitors include, but are not limited to, celecoxib, meloxicam and flosulide. Examples of laxatives include, but are not limited to, dietary fiber and osmotic laxatives such as polyethylene glycol, sorbitol, and lactulose. Examples of anti-diarrheal medicines include, but are not limited to, opiate, opioid or opioid analogs such as loperamide, codeine, diphenoxylate. Examples of anti-spasmodic include, but are not limited to, anticholinergics such as hyoscyamine or dicyclomine. Examples of anti-depressants include, but are not limited to, selective serotonin reuptake inhibitor anti-depressants (SSRIs). A synergistic effect may be achieved by using a combination of the compound utilized according to the invention with the drugs recited above.

In some embodiments, the compound utilized according to the invention and optionally the above recited drug is in combination with a biocompatible excipient provided herein. In some embodiments, the compound utilized according to the invention is present in an amount sufficient to attain a therapeutically effective amount of the compound in the intestinal muscle of the subject upon administration.

In some embodiments, the administration of the compound according to the invention to the subject results in reduced, negligible, or no adverse side effects. Typically, the side effects of common β-adrenergic agonists include, but are not limited to, cardiovascular such as palpitations, peripheral tremors, high heart rate, and low blood pressure; pulmonary edema and hyperglycemia; aggravation of preexisting diabetes and keto acidosis; tremors; nervousness; increased heart rate; palpitations; dizziness; headaches; drowsiness; vomiting; nausea; sweating; muscle cramps; and ECG changes. In some embodiments, the use of the compounds according to the invention reduces or eliminates one or more of the above-noted side effects. It is important to note that such reduced, negligible, or lack of adverse side effects may be especially manifest when comparing the outcomes using the compounds according to the invention with outcomes using other β-adrenergic agonists, including but not limited to one or more of HSR-81, terbutaline, ritodrine, isoproterenol, or pharmaceutically acceptable salts thereof.

Accordingly, in the methods provided herein, the administration of the compound reduces the incidence of one or more adverse side effects in the subject. In some embodiments, the number of incidences of the one or more of adverse side effects in the subject is reduced with the administration of the compound utilized according to the invention as compared to the number of such incidences, which would have been observed in the subject with the administration of terbutaline, ritodrine, or meluadrine. In some embodiments, the β-adrenergic agonist is terbutaline sulfate, ritodrine hydrochloride, or HSR-81. In some embodiments, the administration of the compound utilized according to the invention reduces the incidence of one or more adverse side effects in the subject as compared to terbutaline. In some embodiments, the number of incidences of increased heart rate, increased tremors, decrease in mean blood pressure, or all in the subject after the administration of the compound utilized according to the invention is reduced compared to the number of such incidences, which would have been observed in the subject with the administration of terbutaline. See Lyrenas et al. *Scand J Gastroenterol* 20:1163-1168 (1985); Lyrenas et al. *Scand J Gastroenterol* 28:907-910 (1993).

The reduction of one or more of the adverse side effects by the compound utilized according to the invention is more than 10% reduction; or alternatively more than 20% reduction; or alternatively more than 30% reduction; or alternatively more than 40% reduction; or alternatively more than 50% reduction; or alternatively more than 60% reduction; or alternatively more than 70% reduction; or alternatively more than 80% reduction; or alternatively more than 90% reduction; or alternatively more than 99% reduction; or alternatively complete reduction of the adverse side effect. In some embodiments, the above recited reduction in the one or more of the adverse side effects is as compared to the adverse side effects of other β-adrenergic agonists. In some embodiments, the above recited reduction in the one or more of the adverse side effects is as compared to the adverse side effects of terbutaline.

Typically, the β-adrenergic agonists suffer from a short half life or low bioavailability. In some embodiments, the compounds of the invention have a longer half life or higher bioavailability as compared to other β-adrenergic agonists, such as but not limited to, terbutaline.

3. Compounds Used in the Invention

The compounds that are used in the methods, compositions, and devices of the invention are as follows.

In one aspect, the compound is of formula I:

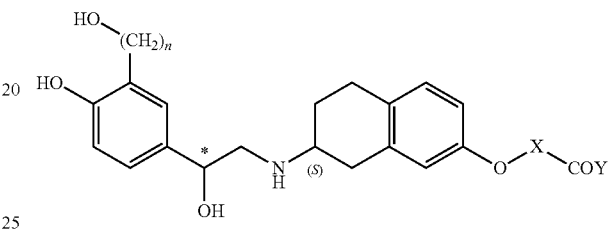

wherein n is an integer selected from 1 or 2;

X is a $C_1$-$C_6$ alkylene group;

Y is —N(R)$_2$ wherein each R is independently selected from hydrogen or $C_1$-$C_6$ alkyl, or two R along with the nitrogen bound thereto join together to form a 3 to 7 membered heterocyclic ring optionally containing an oxygen atom; and \* represents a carbon atom in an R configuration, an S configuration, or a mixture thereof, a metabolite thereof, a prodrug thereof, or a pharmaceutically acceptable salt of any of the foregoing.

In one aspect, the compound is of formula II:

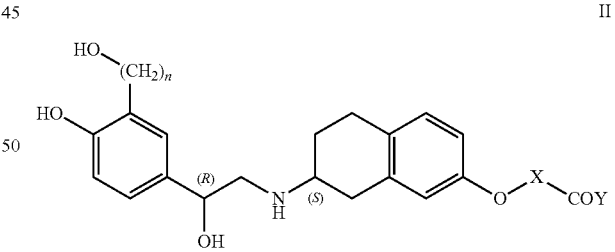

wherein n is an integer selected from 1 or 2;

X is a $C_1$-$C_6$ alkylene group; and

Y is —N(R)$_2$ wherein each R is independently selected from hydrogen or $C_1$-$C_6$ alkyl, or two R along with the nitrogen bound thereto join together to form a 3 to 7 membered heterocyclic ring optionally containing an oxygen atom;

a metabolite thereof, a prodrug thereof, or a pharmaceutically acceptable salt of any of the foregoing.

In one aspect, the compound is of formula III:

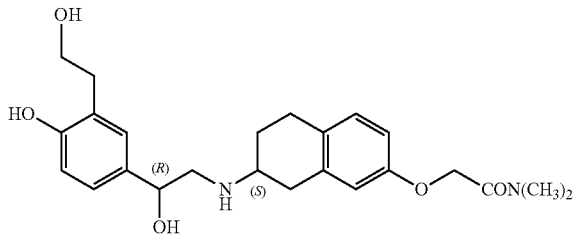

a metabolite thereof, a prodrug thereof, or a pharmaceutically acceptable salt of any of the foregoing.

In one aspect, the metabolite is of formula IV:

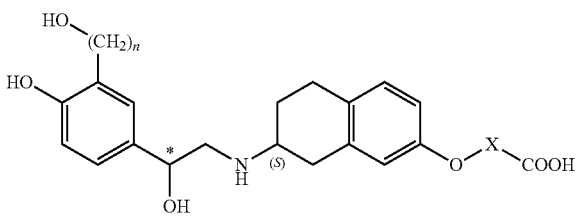

wherein
n is an integer selected from 1 or 2;
X is a $C_1$-$C_6$ alkylene group; and
* represents a carbon atom in an R configuration, an S configuration, or a mixture thereof,
or a pharmaceutically acceptable salt thereof.

In some embodiments, the compound is of formula V:

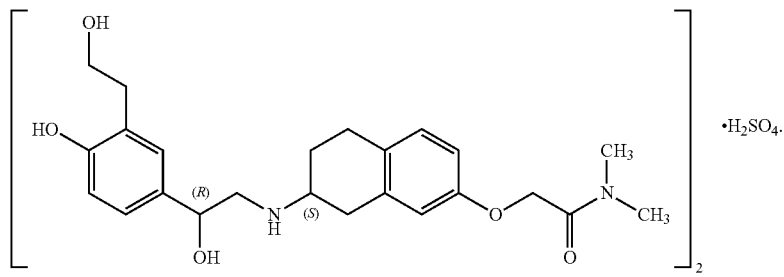

In some embodiments of the above recited aspects, X is a $C_1$-$C_3$ alkylene group. In some embodiments of the above recited aspects, X is a —$CH_2$— group.

In some embodiments of the above recited aspects, Y is —$N(R)_2$ wherein each R is hydrogen.

In some embodiments of the above recited aspects, Y is —$N(R)_2$ wherein each R is $C_1$-$C_6$ alkyl. In some embodiments of the above recited aspects, Y is —$N(R)_2$ wherein each R is $C_1$-$C_2$ alkyl. In some embodiments of the above recited aspects, Y is —$N(R)_2$ wherein each R is methyl. In some embodiments of the above recited aspects, Y is —NHR wherein R is $C_1$-$C_2$ alkyl.

In some embodiments of the above recited aspects, Y is —$N(R)_2$ wherein two R along with the nitrogen bound thereto join together to form a 3 to 7 membered heterocyclic ring optionally containing an oxygen atom.

In some embodiments of the above recited aspects, * represents a carbon atom in R configuration. In some embodiments of the above recited aspects, * represents a carbon atom in S configuration. In some embodiments of the above recited aspects, * represents a carbon atom which is a mixture of R and S configuration.

In some embodiments of the above recited aspects, n is 1. In some embodiments of the above recited aspects, n is 2.

The compounds utilized according to the invention can exist in unsolvated as well as solvated forms, including hydrated forms. In general, the solvated forms, including hydrated forms and the like are equivalent to the unsolvated forms for purposes of the invention.

In some embodiments, the compound is in a form of a prodrug wherein the prodrug is selected from the group consisting of compounds wherein hydroxyl or amine groups are bonded to a group that, when administered to a subject, cleaves to form a free hydroxyl or amine group, respectively. In some embodiments, the prodrug is selected from the group consisting of acetate, formate, benzoate and phosphate ester derivatives of hydroxyl functional group, and acetyl and benzoyl derivatives of amine functional group.

In some embodiments, the compound or the prodrug thereof is in a form of a pharmaceutically acceptable salt thereof wherein the pharmaceutically acceptable salt thereof is an acid addition salt wherein the acid is selected from the group consisting of hydrochloric, sulfuric, phosphoric, acetic, citric, oxalic, malonic, salicyclic, malic, gluconic, fumaric, succinic, ascorbic, maleic, and methanesulfonic acid. In some embodiments, the pharmaceutically acceptable salt thereof is sulfuric acid.

In some embodiments, the compound is a metabolite of a compound of formula I, II, III, IV, or V, where metabolites are as described herein. In some embodiments, the compound is a pharmaceutically acceptable salt of the metabolite of the compound, where pharmaceutically acceptable salts are as described herein.

The compounds of the invention can be synthesized using routine synthetic chemistry known to one skilled in the art. For example, the syntheses of the compounds of the invention and their experimental data are described in U.S. Pat. No. 6,133,266 and U.S. Pat. No. 6,136,852, which are incorporated herein by reference in their entirety.

4. Pharmaceutical Compositions, Devices and Dosages

In one aspect, the compound utilized according to present invention are administered as a composition comprising the compound and a pharmaceutically acceptable carrier. The compounds utilized according to the invention can be administered in admixture with conventional excipients, such as, pharmaceutically acceptable liquid, semi-liquid or solid organic or inorganic carriers, which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring, and/or aromatic substances and the like which do not deleteriously react with the active compounds.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

In some embodiments, the composition is administered as a formulation suitable for parenteral routes of administration, such as intravenous, intramuscular, percutaneous, and subcutaneous administration. For parenteral application, particularly suitable are solutions, preferably oily or aqueous solutions, as well as suspensions, emulsions, or implants, including suppositories.

In a related embodiment, the intravenous formulation comprises approximately 0.20 mg to about 20 mg; or alternatively about 0.20 mg to about 10 mg; or alternatively about 0.20 mg to about 5 mg; or alternatively about 0.20 mg to about 3 mg; or alternatively about 0.20 mg to about 2 mg; or alternatively about 0.20 mg to about 1 mg; of the compound utilized according to the invention in an aqueous delivery system. The aqueous delivery system may comprise about 0.02% to about 0.5% (w/v) of an acetate, phosphate, or citrate buffer. In another aspect, the formulation has a pH of about 3.0 to about 7.0. In a related aspect, the concentration of the compound in the intravenous formulation falls in the range of about 0.15 $\mu$mol/mL to about 0.25 $\mu$mol/mL.

In some embodiments, the subject is administered an amount of the compound in the range of about 3 $\mu$g/kg patient (or about 200 $\mu$g per patient) to about 60 $\mu$g/kg patient (or about 4 mg per patient). The dosage may be administered intravenously as a single bolus injection to the subject, or as single bolus injection followed by a constant infusion for up to 24, 36, 48, or 72 hours, or as a constant infusion for up to 24, 36, 48, or 72 hours. The dosage may be administered subcutaneously or intravenously at intervals not less than 4 hours and for up to 24, 36, 48, or 72 hours. In some embodiments, the subject is administered intravenously for 15 minutes at about 40 $\mu$g/min and then about 45 minutes at about 13 $\mu$g/min. In yet another embodiment, the subjects are those who have been admitted to an emergency room.

In some embodiments, the intravenous formulation is reconstituted from a freeze-dried drug product comprising the compound. In another embodiment, the freeze-dried drug product further comprises carbohydrate and/or polyhydric alcohols. The carbohydrate may be mannose, ribose, trehalose, maltose, inositol, lactose, or the like. The polyhydric alcohols may be sorbitol, mannitol, or the like.

In certain embodiments within the various aspects and embodiments of the present invention, the compound is administered by infusion. In one embodiment, the infusion is performed at a rate of about 3 $\mu$g ($\mu$gm or $\mu$g)/minute to about 60 $\mu$g/min; about 6 $\mu$g/minute to about 30 $\mu$g/minute; about 12 $\mu$g/minute to about 15 $\mu$g/minute; about 7 $\mu$g/minute to about 18 $\mu$g/minute; about 9 $\mu$g/minute; about 13 $\mu$g/minute; and about 16 $\mu$g/minute.

The compound is formulated as a liquid formulation for administration in accordance with the various aspects and embodiments of the present invention. In some embodiments, the liquid formulation comprises the compound in an amount of about 3 $\mu$g/mL to about 60 $\mu$g/mL, about 6 $\mu$g/mL to about 30 $\mu$g/mL, and about 12 $\mu$g/mL to about 30 $\mu$g/mL, and about 15 $\mu$g/mL to about 20 $\mu$g/mL. In another embodiment, the liquid formulation further comprises dextrose. In another embodiment, the liquid formulation is an aqueous formulation. In another embodiment, the liquid formulation is suitable for intravenous injection or infusion.

In the various aspects and embodiments of the present invention, the compound is used as a 2 mg, unit dose, lyophilized drug product. Other unit dose forms in the range of about 0.2 mg to about 20 mg are also contemplated. In one embodiment, the lyophilized drug product further comprises lactose.

In one aspect, the compositions of the invention are delivered topically. Topical administration can involve the use of transdermal administration such as transdermal patches or iontophoresis devices. Dosage forms for topical administration of the compounds and compositions can include creams, sprays, lotions, gels, ointments, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol).

The compositions can also be applied topically using a transdermal system, such as one of an acrylic-based polymer adhesive with a resinous cross-linking agent impregnated with the composition and laminated to an impermeable backing. In some embodiments, the compositions utilized according to the present invention are administered in the form of a transdermal patch, such as in the form of a sustained-release transdermal patch. In some embodiments, the compositions utilized according to the present invention are administered in a form of a five day transdermal patch.

The transdermal patches utilized according to the present invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material.

In some embodiments, the transdermal patches comprise a therapeutically effective amount of the composition of the invention and optionally an antioxidant. Examples of antioxidants include, but are not limited to, hydralazine compounds, glutathione, vitamin C, vitamin E, cysteine, N-acetyl-cysteine, $\beta$-carotene, ubiquinone, ubiquinol-10, tocopherols, coenzyme Q, and the like. Suitable antioxidant enzymes include, but are not limited to, superoxide dismutase, catalase, glutathione peroxidase, and the like. Suitable antioxidants are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996).

In some embodiments, the composition, the transdermal patch, or the delivery device can be a controlled release composition. Non-limiting examples of a suitable biocompatible excipient for applying the compound include a lipophilic carrier or a hydrophilic carrier. Non-limiting examples of a lipophilic carrier include semi-synthetic glycerides of saturated fatty acids. Non-limiting examples of a hydrophilic carrier include polyethylene glycol having an average molecular weight of 6000, polyethylene glycol having an average molecular weight of 1500, polyethylene glycol having an average molecular weight of 400 or mixtures thereof. The biocompatible excipient can also include a muco-adhesive agent such as alginate, pectin, or cellulose derivative. The biocompatible excipient can also include a penetration enhancer such as bile salts, organic solvents, ethoxydiglycol, or interesterified stone oil.

In one embodiment of the invention, the excipient comprises between about 60 to 90% by weight lipophilic carrier, between about 5 to 25% mucoadhesive agent, and between about 5 to 20% penetration enhancer. In another embodiment of the invention, the excipient comprises between about 60 to 90% by weight hydrophilic carrier, between about 5 to 25% muco-adhesive agent, and between about 5 to 20% penetration enhancer. In another embodiment of the invention, the patch or the drug delivery device comprises a standard fragrance free lotion formulation. In another embodiment, the biocompatible excipient can include glycerin, mineral oil, polycarbophil, carbomer 934P, hydrogenated palm oil, glyceride, sodium hydroxide, sorbic acid, and purified water.

In some embodiments, the transdermal patch contains, about 5-5000 mg; or alternatively about 5-4000 mg; or alternatively about 5-3000 mg; or alternatively about 5-2000 mg; or alternatively about 5-1000 mg; or alternatively about 5-500 mg; or alternatively about 5-100 mg; or alternatively about 5-50 mg, of the compound utilized according to the invention. In some embodiments, the transdermal patch administers a sustained release of the compound utilized according to the invention over a period of from about few months to about few weeks; or from about few weeks to about few days; or 6 days; or 5 days; or 4 days; or 3 days; or 2 days; or 1 day. The transdermal patch may be replaced once a day, once a week, or once a month for effective treatment.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein the active compound is protected with differentially degradable coatings, e.g., by microencapsulation, multiple coatings, etc. Suitable for oral administration are, inter alia, tablets, dragees, capsules, pills, granules, suspensions and solutions. Each unit dose, e.g., each tablespoon of liquid or each tablet, or dragee contains, for example, 5-5000 mg of each active agent or the compound utilized according to the invention.

In some embodiments, the pharmaceutically acceptable carrier is a bioadhesive carrier. In some aspects, the bioadhesive carrier is a cross-linked water-insoluble but water-swellable polycarboxylic acid polymer. The cross-linked polycarboxylic acid polymer formulation, is generally described in U.S. Pat. No. 4,615,697 (hereinafter "the '697 patent"), which is incorporated herein by reference. In general, at least about eighty percent of the monomers of the polymer in such a formulation may contain at least one carboxyl functionality. The cross-linking agent may be present at such an amount as to provide enough bioadhesion to allow the system to remain attached to the target epithelial surfaces for a sufficient time to allow the desired dosing to take place. This preferred level of bioadhesion can be attained when the cross-linking agent is present at about 0.1 to 6.0 weight percent of the polymer, with about 1.0 to 2.0 weight percent being most preferred, as long as the appropriate level of bioadhesion results. Bioadhesion can also be measured by commercially available surface tensiometers utilized to measure adhesive strength.

The polymer formulation can be adjusted to control the release rate of the compounds of the invention, by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents. A preferred polymer for use in such a formulation is Polycarbophil, U.S.P., which is commercially available from B.F. Goodrich Specialty Polymers of Cleveland, Ohio under the trade name NOVEON®-M1. The United States Pharmacopeia, 1995 edition, United States Pharmacopeial Convention, Inc., Rockville, Md., at pages 1240-41, indicates that polycarbophil is a polyacrylic acid, cross-linked with divinyl glycol. It has also been used as a base for compositions with other active substances such as progesterone (Crinone®) (see U.S. Pat. No. 5,543,150) and Nonoxynol-9 (Advantage-S) (see U.S. Pat. No. 5,667,492). Other useful bioadhesive polymers that may be used in such a drug delivery system formulation are mentioned in the '697 patent. For example, these include polyacrylic acid polymers cross-linked with, for example, 3,4-dihydroxy-1,5-hexadiene, and polymethacrylic acid polymers cross-linked with, for example, divinyl benzene.

Typically, these polymers may not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

The bioadhesive formulation may be in the form of a gel, cream, tablet, pill, capsule, suppository, film, or any other pharmaceutically acceptable form that adheres to the mucosa and does not wash away easily. Different formulations are further described in the '697 patent, which is incorporated herein by reference.

Additionally, the additives taught in the '697 patent may be mixed in with the cross-linked polymer in the formulation for maximum or desired efficacy of the delivery system or for the comfort of the patient. Such additives include, for example, lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

The compound utilized according to the invention or the other optional drug can be administered as an admixture or as a separate unit dosage form, either simultaneously therewith or at different times during the day from each other. The compound and the optional drug are preferably administered at least once daily (unless administered in a dosage form which delivers the active agents continuously) and more preferable several times daily, e.g., in 2 to 6 divided doses. The typical dose is about 0.5 to 1000 mg of each active agent.

A lower dosage regimen can be initiated and the dosage can be increased until a positive effect is achieved or a higher dosage regimen can initially be utilized, e.g., in a crisis situation, and the dosages regulated downward as relief from the symptoms is achieved.

In some embodiments, the method of the invention comprises rectal insertion of a device comprising a compound utilized according to the invention for treatment of IBS in a pharmaceutically acceptable, non-toxic carrier. The composition is combined with a suitable delivery device or system which permits the rectal delivery of the drug. Examples of the drug delivery system include, but are not limited to, pessary, tablet, suppository, sponge, bioadhesive tablet, bioadhesive microparticle, cream, lotion, foam, ointment, solution and gel. Alternatively, it can be a coating on a suppository wall or a sponge or other absorbent material impregnated with a liquid drug containing solution, lotion, or suspension of bioadhesive particles. Any form of drug delivery system which will effectively deliver the treatment agent to the rectal epithelium is intended to be included within the scope of this invention.

In some embodiments, the compound and an optional drug are in the form of a microsphere for enhancing uptake of the compound and the drug. The microparticles have a diameter of 10-100 pm and can be prepared from starch, gelatin, albumin, collagen, or dextran.

The compound can also be incorporated into creams, lotions, foams, paste, ointments, and gels which can be applied to the vagina using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water. Suitable non-toxic pharmaceutically acceptable systems for use in the compositions of the present invention will be apparent to those skilled in the art of pharmaceutical formulations and examples are described in REMINGTON'S Pharmaceutical Sciences, 19th Edition, A. R. Gennaro, ed., 1995. The choice of suitable carriers will depend on the exact nature of the particular dosage form desired, e.g., whether the active ingredient(s) is/are to be formulated into a cream, lotion, foam, ointment, paste, solution, or gel, as well as on the compound.

The excipient can be an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

In certain embodiments within the various aspects and embodiments of the present invention, the compound is administered in an amount of about 2000 μg (or 2 mg), about 1200 μg, about 1000 μg, about 800 μg, about 600 μg, about 450 μg, about 400 μg, about 250 μg, and about 200 μg (or 0.2 mg). In other embodiments, the compound is administered in an amount of about 200 μg to about 2000 μg.

In certain embodiments within the various aspects and embodiments of the present invention, the compound is administered once a day, twice a day or thrice a day up to a period of days, months or years, until relief from symptoms is achieved. The compound may be administered at various rates of administration, for various periods of time.

The following examples are provided to illustrate select embodiments of the invention as disclosed and claimed herein.

EXAMPLES

The compound MN-221 in the examples provided herein, refers to the sulfate salt of formula:

(−)-bis(2-{[(2S)-2-({(2R)-2-hydroxy-2-[4-hydroxy-3-(2-hydroxyethyl)phenyl]ethyl}amino)-1,2,3,4-tetrahydronaphthalen-7-yl]oxy}-N,N-dimethyl-acetamide) monosulfate.

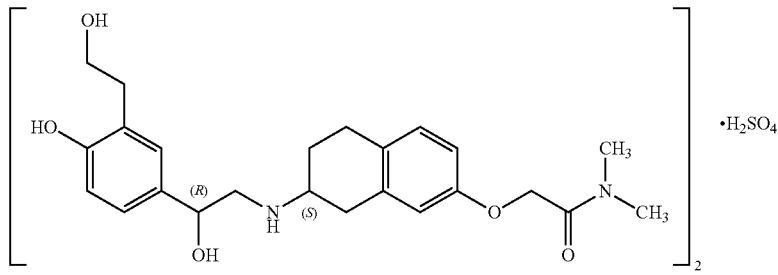

MN-221 can be synthesized according to methods reported in literature. See, e.g., U.S. Pat. No. 6,133,266, which is incorporated herein by reference in its entirety.

Example 1

Effects of MN-221 on Rectosigmoid Motility

In this study, subjects with the irritable bowel syndrome (IBS) are studied with regard to the effects of MN-221 on rectosigmoid motility.

Materials and Methods
Subjects

Men and women aged 24-52 years are included in the study. The diagnosis of IBS is made on the basis of the following criteria: 1) symptoms lasting more than few months; 2) abdominal pain with or without relation to meals; 3) constipation or a combination of diarrhea and constipation; 4) normal colonic barium enema and sigmoidoscopy; 5) negative test for lactose intolerance; and 6) negative finding on stool culture.

The subjects are all symptomatic at the time of the study. The subjects are taking no medications of significant importance for intestinal motility. Informed consent is obtained from each subject.

Experimental Design

After a 12 hours fast, all subjects undergo sigmoidoscopy without air insufflations. A probe with one to three polyethylene catheters is inserted through the sigmoidoscope so that the proximal catheter is about 18-20 centimeter (cm) from the anal margin, the tip of the second catheter about 5 cm below, and the third catheter is positioned just inside the internal sphincter. An about 5-cm-long balloon surrounds each of the two distal catheters. The distal balloon is inflated with about 20 milliliter (mL) of air to prevent the device from moving in the distal direction. The balloon in the upper rectum, connected to the middle catheter, is kept inflated with about 80 ml of air in 10 of the subjects and with about 60 mL in the other 2 subjects throughout the recording sessions. Each subject has the same balloon volume during the three examinations.

Intra-luminal pressure is measured from the proximal rectal balloon and the sigmoid catheter (inside diameter, about 1.67 millimeter (mm)), which is open tipped with a side orifice of about 1.5 mm diameter.

The catheter is continuously perfused with body-temperature water at 3.5 mL/h by means of an infusion pump. Pressure is transmitted to transducers (e.g., Statham P 23 Db, Statham Instruments, Hato Ray, Puerto Rico) and recorded on a Grass RPS 7C polygraph (e.g., Grass Instrument Co., Quincy, Mass.). To determine motility, the area under the pressure curves is continuously determined by integrators (such as, e.g., Grass 7P 10). As an index of contractile activity, the total area minus the area under an estimated basal pressure line is used. The principle for motility calculation is described in detail in Abrahamsson et al. *Dig Dis Sci* 1983, 28, 590-594.

Motility index is expressed as kPa×min (1 kPa×min=7.5 mm Hg×min). The study is randomized and double blinded. Each subject is investigated on 3 different days with not less than 5 days between each investigation to avoid any possible influence of an earlier drug infusion. After an initial rest period of 30 minutes (min), pressure is quantified for three periods of 25 min. The first period, designated the control period, is preceded by saline infusion, 1 mL/min, for 5 min. The following two test periods are each preceded by an infusion of 0.25 mg MN-221 intravenously to a total amount of 0.50 mg on the 1st day, 1.0 mg on the 2nd day, and 5 ml placebo (plus 5 mL saline) on the 3rd day.

The blood pressure and heart rate are measured by a sphygmomanometer 10 and 25 min after the end of each drug infusion. Blood samples are drawn from a venous cannula at the same time for determination of the plasma concentrations of the drugs. The code for the drug is not broken until calculations of motility indices are completed.

Statistical Analysis

Results are expressed as the mean±SEM. Differences between control and test periods are tested with Wilcoxon's rank sign test for paired data.

Analytical Methods

The plasma concentration of MN-221 is determined by liquid chromatography and mass spectrometry.

Results
Sigmoid Motility

Basal Conditions and Effects of Placebo.

The sigmoid motility index varies considerably between the subjects and in the same subject on the different days. The motor activity consists mainly of three different types of motor waves. The commonest form is pressure waves with a frequency of 2-3/min. The amplitude is generally between 1 and 4 kPa, and the duration of each wave 10-25 seconds (sec). Between these prominent waves, other waves with low amplitude and a frequency of 6-8/min may occur. In periods with high motor activity, the base-line pressure may often increase, with clusters of 3/min waves and superimposed small 7/min waves. After placebo infusion, contractile activity has a tendency to increase in wave frequency, duration, and amplitude. Results show that sigmoid motility increases in subjects.

Effects of MN-221.

During the control period before MN-221 infusion the motility index is calculated. After 0.50 milligram (mg) of MN-221 administered intravenously, the mean motility index decreases by more than about 50% compared with the control period. After MN-221 in a total dose of 1.0 mg is administered intravenously, the motility index decreases further. Results show that sigmoid motility decreases in subjects.

Rectal Motility

Rectal motility, as registered with the proximal rectal balloon, shows substantial individual variations in motility between each day of registration. One third of all control periods had a motility close to zero. This pattern is not changed after infusion of MN-221.

Systemic Effects

Placebo infusion is not followed by any significant changes in heart rate or in blood pressure compared with the preceding control period. After MN-221 infusion to a total of 0.50 mg intravenously, no significant increase in the systolic blood pressure; decrease in the diastolic blood pressure; and/or increase in the heart rate is observed. MN-221 infusion to a total of 1.0 mg intravenously results in no significant increase in systolic blood pressure; decrease in diastolic blood pressure; and/or increase in heart rate. No major complaints or discomfort are noted among the subjects after infusion of MN-221. These results show that the use of MN-221 is associated with little to no adverse side effects compared with the use of terbutaline, which is associated with an undesirable incidence of significant adverse side effects, including increase in systolic blood pressure and the heart rate.

Plasma Concentrations of the Drugs

The drug infusions are followed by a dose-dependent increase in plasma levels of the drugs.

Discussion

The present study shows that administration of MN-221 significantly decreases sigmoid colonic motility in subjects with the IBS. After placebo infusion, motility has a tendency to increase during the test period, further emphasizing the inhibitory effect of MN-221. The plasma concentrations of MN-221 are observed to be within the therapeutic levels used in clinical practice.

Rectal motility is registered from an air inflated balloon. The inflated volume used in the study is chosen so as not to reach the low pain threshold for rectal distention. None of the subjects complains of pain during balloon inflation. Thus, variation in distention-induced discomfort is not likely to have influenced the response to the drugs. Statistical comparison between the test and control periods do not show any change after each drug.

This study suggests an inhibitory influence on motility along the whole gut by MN-221.

Example 2

Effects of MN-221 on Human Esophageal Peristalsis

Subjects with irritable bowel syndrome may complain of upper gastrointestinal symptoms, including heartburn and dysphagia. MN-221 inhibits esophageal peristalsis and tone of the lower esophageal sphincter in subjects suffering from IBS.

This study investigates the inhibitory influence of beta-2-adrenergic stimulation by MN-221 on esophageal motility with little to no incidence of significant adverse side effects. In the study, esophageal peristalsis is studied in subjects suffering from IBS. The subjects have no history of gastrointestinal or cardiovascular disease. Subjects are considered to have the irritable bowel syndrome if they have an abdominal pain with or without diarrhea or constipation. Relief of pain by defecation, abdominal distension, a feeling of incomplete evacuation, and/or a response to a high-residue diet are taken as useful additional symptoms. The blood picture, erythrocyte sedimentation rate, and results of sigmoidoscopy, rectal biopsy, and barium enema are normal in all subjects. The symptoms of the subjects, including dysphagia and heartburn, are recorded on data sheets for correlation with manometric findings.

Each subject is orally given MN-221, 5 mg three times daily, for 10 days. The subjects are studied before medication (basal), on days 3 and 10 during the medication, and 1 week after withdrawal of the drug. At each session esophageal peristaltic pressure, heart rate, and finger tremor are assessed.

Esophageal Measurements

Manometric studies are performed with a triple-lumen tube with each channel perfused with water, 0.5 ml/min, via a low-compliance capillary system. The channels are connected to pressure transducers with recording on a Grass polygraph. The pressure recording sites are about 8 cm apart. After an overnight fast, the subjects are examined seated in a standardized position with the manometric probe inserted via the nasal route. The probe is placed with the distal recording point about 2 cm proximal to the lower esophageal sphincter (LES). Thus, pressure is recorded about 18 cm proximal to the LES (proximal esophagus), about 10 cm proximal to the LES (middle esophagus), and about 2 cm proximal to the LES (distal esophagus).

After a resting period of 20 min., esophageal peristalsis in response to 20 wet swallows (water bolus of 5 ml, room temperature) is recorded. At least 30 sec are allowed between each bolus. Each recording curve is coded and read by one investigator who is not aware of the subject's study day. The amplitude of the peristaltic pressure waves is measured at each recording point, and an individual mean value for the 20 swallows is calculated for each examination.

Extra Intestinal Recordings

At each session, heart rate is recorded in the resting subject and calculated as a mean value for 2 min. Finger tremor are assessed with an optical method (e.g., Opto-Tremor Graph, Draco), and the middle finger of the right hand is chosen for measurement. Tremor values are displayed as digital data and given as the sum of the length of movements in millimeters per minute.

MN-221 Analyses

At each session, venous blood samples are taken immediately after the last test swallow. After centrifugation, samples are stored at $-20°$ C. until analysis. The plasma concentration of MN-221 is determined by liquid chromatography plus mass spectrometry.

Adverse Reactions

Tachycardia and tremor are classified in accordance with a four-degree scale: absent, slight (not disturbing), moderate (disturbing, but not disabling), and severe (disabling).

Results

Esophageal Peristalsis

Oral administration of MN-221 results in a significant decrease of esophageal peristaltic pressure. The decrease is evident in proximal, middle and/or distal esophagus. One week later, there is still a trend towards decreased peristaltic pressure.

Heart Rate and Tremor

The extraintestinal variables, heart rate and finger tremor, do not change during MN-221 medication. Thus, both heart rate and tremor stay substantially the same as before medication. At the end of the medication period, such as on day 10, no significant changes in the heart rate or finger tremor are seen. There is no substantial indication of the tolerance of the subjects toward MN-221.

It is concluded that oral medication with MN-221 inhibits esophageal peristalsis in subjects with IBS. These results show that the use of MN-221 is associated with little to no adverse side effects compared with the use of terbutaline, which is associated with an undesirable incidence of significant adverse side effects, including increase in the heart rate and finger tremors. The results also indicate no significant development of esophageal tolerance to MN-221 as compared to terbutaline which is associated with the development of esophageal tolerance with continued medication.

Example 3

Treatment of Irritable Bowel Syndrome Using MN-221

A 35-year-old male patient complains of symptoms associated with IBS, including diarrhea with discharge of mucus and blood, cramping abdominal pain, and/or inflammation and edema of the mucous membrane with patches of ulceration. The patient is treated with tablets containing 5 mg of MN-221, three times per day, for at least two months. After this time period, the patient reports positive effects, including a reduction in the symptoms. Similar positive results are observed for other male or female patients complaining of one or more of the similar symptoms attributable to IBS.

Example 4

Treatment of Irritable Bowel Syndrome Using MN-221

Previous reports have demonstrated that intravesical instillation of ovalbumin in sensitized guinea pigs increases bladder contractions. See, Ahluwalia et al. "Ovalbumin-induced neurogenic inflammation in the bladder of sensitized rats" *Br. J. Pharmacol.* (1998) 124:190-6. In this study, MN-221 is shown to be beneficial in suppressing ovalbumin-induced bladder contractions in a rat model of inflammation-induced bladder hyperactivity. This rat model serves as an animal model for irritable bowel syndrome.

Methods:

A. Sensitization of Rats:

Sprague-Dawley rats (n=50; 200±250 g) are utilized for this study. The animals are divided into 5 groups (n=10). The first group serves as a control and second group is sensitized with ovalbumin (OA). The third, fourth, and fifth groups are also sensitized as described but are subjected to oral gavaging with MN-221 prior to acute ovalbumin challenge.

Sensitization of the animals is accomplished with an intraperitoneal injection of a mixture of 1 mg OA and 100 mg aluminum hydroxide suspended in 1 mL of saline. Fourteen days later, these sensitized rats are anaesthetized with a subcutaneous injection of urethane (1.2 g/kg) for intravesical OA (10 mg/mL) administration and evaluation of bladder hyperactivity. The animals in group 1 receive saline (control), group 2 animals receive about 2 mL of OA (10 mg/mL OA in sterile saline) and groups 3-5 animals receive oral MN-221 (10, 30, 50 mg/kg in gum acacia suspension) 60 minutes prior to acute OA challenge (2 mL of 10 mg/mL OA).

B. Evaluation of Bladder Overactivity:

All animals are subjected to evaluation of bladder hyperactivity. Briefly, a 1 cm incision is made along the centerline of the lower ventral abdomen. The bladder is exteriorized, and catheterized by means of a polyethylene tube (e.g., PE 50, Clay Adams) inserted into the bladder dome and sutured in place using a 2-0 braided silk suture. The bladder is returned to the abdomen, with the catheter line escaping through the incision. The catheter is then connected to a pressure transducer (e.g., UFI, Morro Bay, Calif.) and in turn, connected to an infusion pump (e.g., Harvard Apparatus, Mass.). During the continuous filling bladder cystometry, the pressure is recorded with the transducer using the program LabVIEW (National Instruments, Tex.).

For cystometry (See, Chuang et al. "Intravesical protamine sulfate and potassium chloride as a model for bladder hyperactivity" *Urology* (2003) 61:664-70), the bladder is first infused with warm 0.9% saline (37° C.) at 40 µL/min (2.4 mL/hr) and at least 20 minutes of stable voiding cycles are recorded during infusion. This process is followed by intravesical infusion of OA (10 mg/mL) and bladder contractions are recorded. Frequency of contractions (voids), inter-contractile interval (ICI), and non-voiding contractions (NVC) are calculated from these recordings.

Results:

Tracings of bladder cystometrograms (CMGs) of treatment groups are compared. Infusion of intact rat bladder with 0.9% saline results in normal and comparable numbers of voids and NVC. In OA sensitized rats, intravesical OA (10 mg/mL) infusion results in an increase in NVC relative to non-sensitized saline infusion values. Pre-treatment with MN-221 results in dose-dependent inhibition of OA-induced changes in NVC and ICI. No significant differences are observed in voiding frequency between control (group 1) and different treatment groups (2-5).

These studies indicate that acute intravesical challenge of OA-sensitized rats causes contractions of bladder smooth muscle leading to a significant increase in NVC and a decrease in ICI. Pre-treatment with MN-221 produces a significant protection against these OA-induced changes. Similar outcomes are expected for the pre-treatment with the metabolite of MN-221.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for treatment of irritable bowel syndrome or amelioration of a symptom thereof in a subject, comprising administering to said subject an effective amount of a compound of formula I:

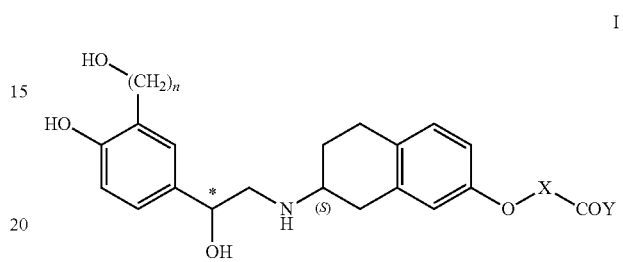

wherein n is an integer selected from 1 or 2;

X is a $C_1$-$C_6$ alkylene group;

Y is —$N(R)_2$ wherein each R is independently selected from hydrogen or $C_1$-$C_6$ alkyl, or two R along with the nitrogen bound thereto join together to form a 3 to 7 membered heterocyclic ring optionally containing an oxygen atom; and

* represents a carbon atom in an R configuration, an S configuration, or a mixture thereof, a metabolite thereof, a prodrug thereof, or a pharmaceutically acceptable salt of any of the foregoing, wherein the administration of the compound reduces the incidence of one or more side effects in the subject compared to the number of such incidences, which would have been observed in the subject with the administration of terbutaline, ritodrine, or meluadrine.

2. The method of claim 1, wherein the compound is of formula II:

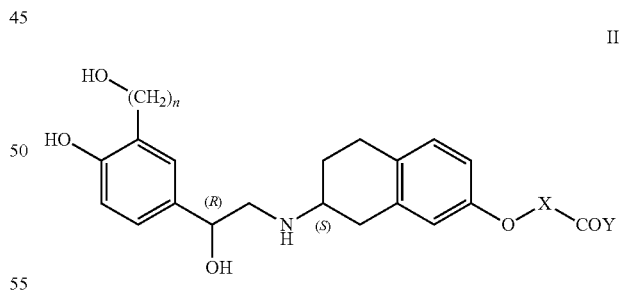

wherein n is an integer selected from 1 or 2;

X is a $C_1$-$C_6$ alkylene group; and

Y is —$N(R)_2$ wherein each R is independently selected from hydrogen or $C_1$-$C_6$ alkyl, or two R along with the nitrogen bound thereto join together to form a 3 to 7 membered heterocyclic ring optionally containing an oxygen atom;

a metabolite thereof, a prodrug thereof, or a pharmaceutically acceptable salt of any of the foregoing.

3. The method of claim 1, wherein the compound is of formula III:

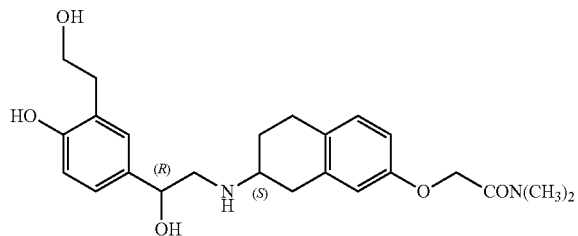

a metabolite thereof, a prodrug thereof, or a pharmaceutically acceptable salt of any of the foregoing.

4. The method of claim 1, wherein the metabolite is of formula IV:

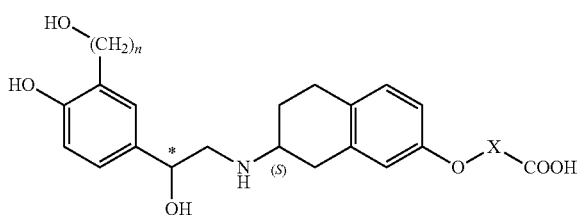

wherein
n is an integer selected from 1 or 2;
X is a $C_1$-$C_6$ alkylene group; and
* represents a carbon atom in an R configuration, an S configuration, or a mixture thereof, or a pharmaceutically acceptable salt thereof.

5. A method for treatment of irritable bowel syndrome or amelioration of a symptom thereof in a subject, comprising administering to said subject an effective amount of a compound of formula V:

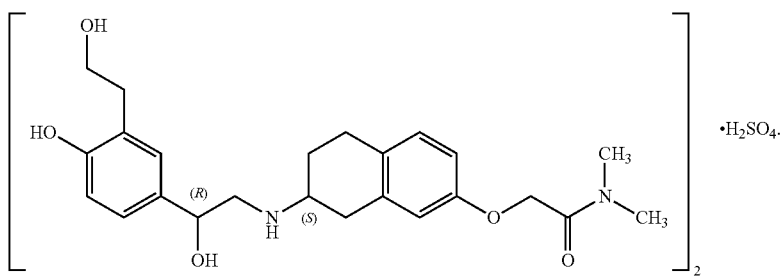

6. The method of claim 1, wherein the subject is a female or male mammal.

7. The method of claim 1, further comprising administering to the subject one or more of a drug selected from the group consisting of non-steroidal anti-inflammatory drug, antibiotic, probiotics, anti-prostaglandin, COX-2 inhibitor, local anesthetic, laxative, anti-diarrhea medicine, anti-spasmodic, and anti-depressant.

8. The method of claim 7, wherein the drug is administered concomitantly or sequentially to said subject.

9. The method of claim 1, wherein the administration is oral.

10. The method of claim 9, wherein the compound is in a form of a tablet, capsule, gel or solution.

11. The method of claim 1, wherein the administration is parenteral selected from intravenous, intramuscular, intraarterial, percutaneous, or subcutaneous.

12. The method of claim 1, wherein the administration is transdermal.

13. The method of claim 1, wherein the prodrug is selected from the group consisting of compounds wherein hydroxyl or amine groups are bonded to a group that, when administered to a subject, cleaves to form a free hydroxyl or amine group, respectively.

14. The method of claim 1, wherein the prodrug is selected from the group consisting of acetate, formate, benzoate and phosphate ester derivatives of hydroxyl functional group, and acetyl and benzoyl derivatives of amine functional group.

15. The method of claim 1, wherein the pharmaceutically acceptable salt is an acid addition salt wherein the acid is selected from the group consisting of hydrochloric, sulfuric, phosphoric, acetic, citric, oxalic, malonic, salicyclic, malic, gluconic, fumaric, succinic, ascorbic, maleic, and methanesulfonic acid.

16. The method of claim 1, wherein the compound is in a composition comprising a pharmaceutically acceptable carrier.

17. The method of claim 1, wherein the compound is administered in a dose of about 0.0001 to about 500 mg per kilogram of body weight per day.

18. The method of claim 1, wherein the one or more adverse side effects are selected from palpitations; peripheral tremors; increased heart rate; decreased blood pressure; pulmonary edema; hyperglycemia; aggravation of preexisting diabetes; aggravation of preexisting keto acidosis; tremors; nervousness; dizziness; headaches; drowsiness; vomiting; nausea; sweating; muscle cramps; and electrocardiogram (ECG) changes.

19. The method of claim 1, wherein the number of incidences of increased heart rate, increased tremors, decrease in mean blood pressure, or all in the subject is reduced compared to the number of such incidences, which would have been observed in the subject with the administration of terbutaline.

* * * * *